(12) United States Patent
Song (10) Patent No.: US 7,504,235 B2
(45) Date of Patent: Mar. 17, 2009

(54) ENZYME DETECTION TECHNIQUE

(75) Inventor: Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 343 days.

(21) Appl. No.: 11/217,097

(22) Filed: Aug. 31, 2005

(65) Prior Publication Data

US 2007/0048815 A1 Mar. 1, 2007

(51) Int. Cl.
C12Q 1/44 (2006.01)

(52) U.S. Cl. ........................................................ 435/19

(58) Field of Classification Search ........................ None
See application file for complete search history.

(56) References Cited

U.S. PATENT DOCUMENTS

| | | |
|---|---|---|
| 3,634,198 A | 1/1972 | Truhan |
| 3,817,705 A | 6/1974 | Stein et al. |
| 4,299,917 A | 11/1981 | Berger et al. |
| 4,434,235 A | 2/1984 | Rabi et al. |
| 4,622,298 A | 11/1986 | Mansour et al. |
| 4,631,255 A | 12/1986 | Takino et al. |
| 4,637,979 A | 1/1987 | Skjold et al. |
| 4,657,855 A | 4/1987 | Corey et al. |
| 4,704,460 A | 11/1987 | Corey |
| 4,742,011 A | 5/1988 | Blake et al. |
| 4,743,560 A | 5/1988 | Campbell et al. |
| 4,748,116 A | 5/1988 | Simonsson et al. |
| 4,806,423 A | 2/1989 | Hugl et al. |
| 4,814,271 A | 3/1989 | Hugl et al. |
| 4,835,099 A | 5/1989 | Mize et al. |
| 4,889,816 A | 12/1989 | Davis et al. |
| 4,904,583 A | 2/1990 | Mapes et al. |
| 4,920,046 A | 4/1990 | McFarland et al. |
| 4,954,435 A | 9/1990 | Krauth |
| 4,956,302 A | 9/1990 | Gordon et al. |
| 4,978,625 A | 12/1990 | Wagner et al. |
| 4,980,298 A | 12/1990 | Blake et al. |
| 5,073,340 A | 12/1991 | Covington et al. |
| 5,075,077 A | 12/1991 | Durley, III et al. |
| 5,075,078 A | 12/1991 | Osikowicz et al. |
| 5,120,643 A | 6/1992 | Ching et al. |
| 5,149,622 A | 9/1992 | Brown et al. |
| 5,185,127 A | 2/1993 | Vonk |
| 5,208,143 A | 5/1993 | Henderson et al. |
| 5,252,459 A | 10/1993 | Tarcha et al. |
| 5,275,785 A | 1/1994 | May et al. |
| 5,415,994 A | 5/1995 | Imrich et al. |
| 5,428,690 A | 6/1995 | Bacus et al. |
| 5,464,739 A | 11/1995 | Johnson et al. |
| 5,468,236 A | 11/1995 | Everhart et al. |
| 5,512,450 A | 4/1996 | Johnson et al. |
| 5,516,700 A | 5/1996 | Smith et al. |
| 5,573,919 A | 11/1996 | Kearns et al. |
| 5,591,645 A | 1/1997 | Rosenstein |
| 5,602,040 A | 2/1997 | May et al. |
| 5,610,077 A | 3/1997 | Davis et al. |
| 5,622,871 A | 4/1997 | May et al. |
| 5,656,503 A | 8/1997 | May et al. |
| 5,663,044 A | 9/1997 | Noffsinger et al. |
| 5,670,381 A | 9/1997 | Jou et al. |
| 5,714,389 A | 2/1998 | Charlton et al. |
| 5,750,359 A | 5/1998 | Huh et al. |
| 5,786,137 A | 7/1998 | Diamond et al. |
| 5,788,863 A | 8/1998 | Milunic |
| 5,798,273 A | 8/1998 | Shuler et al. |
| 5,945,281 A | 8/1999 | Prabhu |
| 5,989,924 A | 11/1999 | Root et al. |
| 5,989,926 A | 11/1999 | Badley et al. |
| 5,998,221 A | 12/1999 | Malick et al. |
| 6,004,821 A | 12/1999 | Levine et al. |
| 6,057,165 A | 5/2000 | Mansour |
| 6,077,669 A | 6/2000 | Little et al. |
| 6,124,107 A | 9/2000 | Humes et al. |
| 6,130,100 A | 10/2000 | Jobling et al. |
| 6,133,048 A | 10/2000 | Penfold et al. |
| 6,156,271 A | 12/2000 | May |
| 6,187,269 B1 | 2/2001 | Lancesseru et al. |
| 6,194,220 B1 | 2/2001 | Malick et al. |
| 6,194,221 B1 | 2/2001 | Rehg et al. |
| 6,197,537 B1 | 3/2001 | Rao et al. |
| 6,203,496 B1 | 3/2001 | Gael et al. |
| 6,235,464 B1 | 5/2001 | Henderson et al. |

(Continued)

FOREIGN PATENT DOCUMENTS

EP 0698600 A1 2/1996

(Continued)

OTHER PUBLICATIONS

Lebovics et al. Leukocyte esterase activity in effusion fluid of patients with otitis media, 1993 108(3):248-250.*

(Continued)

*Primary Examiner*—Jon P Weber
*Assistant Examiner*—Bin Shen
(74) *Attorney, Agent, or Firm*—Dority & Manning, P.A.

(57) ABSTRACT

A diagnostic test kit for detecting the presence or absence of an enzyme (e.g., leukocyte esterase) within a test sample is provided. The test kit comprises a substrate that is capable of being cleaved in the presence of the enzyme to release a nucleophilic aromatic compound. The kit also comprises a lateral flow device that comprises a chromatographic medium. The chromatographic medium defines a detection zone within which is contained a first reagent (e.g., diazonium ion) that is capable of reacting with the nucleophilic aromatic compound to form a second reagent (e.g., aromatic azo compound). The second reagent exhibits a color that is different than the color of the first reagent. The lateral flow device also includes an absorbent material located adjacent to the chromatographic medium, the absorbent material receiving the test sample after flowing through the chromatographic medium.

38 Claims, 1 Drawing Sheet

U.S. PATENT DOCUMENTS

| | | |
|---|---|---|
| 6,274,324 B1 | 8/2001 | Davis et al. |
| 6,294,391 B1 | 9/2001 | Badley et al. |
| 6,352,862 B1 | 3/2002 | Davis et al. |
| 6,399,398 B1 | 6/2002 | Cunningham et al. |
| 6,485,926 B2 | 11/2002 | Nemori et al. |
| 6,503,725 B2 | 1/2003 | Huh |
| 6,514,769 B2 | 2/2003 | Lee |
| 6,524,864 B2 | 2/2003 | Fernandez de Castro |
| 6,528,652 B1 | 3/2003 | Huh |
| 6,537,823 B1 | 3/2003 | Smith |
| 6,573,108 B1 | 6/2003 | Hardman et al. |
| 6,605,447 B2 | 8/2003 | Weiss et al. |
| 6,627,459 B1 | 9/2003 | Tung et al. |
| 6,653,149 B1 | 11/2003 | Tung et al. |
| 6,669,908 B2 | 12/2003 | Weyker et al. |
| RE38,430 E | 2/2004 | Rosenstein |
| 6,689,618 B1 | 2/2004 | Chen |
| 6,818,452 B2 | 11/2004 | Wong |
| 6,875,185 B2 | 4/2005 | Wong et al. |
| 6,951,631 B1 | 10/2005 | Catt et al. |
| 6,951,730 B2 | 10/2005 | Small et al. |
| 6,979,576 B1 | 12/2005 | Cheng et al. |
| 7,044,919 B1 | 5/2006 | Catt et al. |
| 7,052,831 B2 | 5/2006 | Fletcher et al. |
| 2002/0042149 A1 | 4/2002 | Butlin et al. |
| 2002/0045273 A1 | 4/2002 | Butlin et al. |
| 2002/0137117 A1 | 9/2002 | Small et al. |
| 2003/0119073 A1 | 6/2003 | Quirk et al. |
| 2003/0124739 A1 | 7/2003 | Song et al. |
| 2004/0151632 A1 | 8/2004 | Badley et al. |
| 2004/0161859 A1 | 8/2004 | Guo et al. |
| 2005/0029924 A1 | 2/2005 | Okay et al. |
| 2005/0036148 A1 | 2/2005 | Phelan et al. |
| 2005/0037510 A1 | 2/2005 | Shamrock et al. |
| 2005/0109951 A1 | 5/2005 | Fish et al. |
| 2005/0112085 A1 | 5/2005 | MacDonald et al. |
| 2005/0112635 A1 | 5/2005 | Gentle et al. |
| 2005/0124072 A1 | 6/2005 | Boga et al. |
| 2005/0191704 A1 | 9/2005 | Boga et al. |
| 2006/0003336 A1 | 1/2006 | Song et al. |
| 2006/0003394 A1 | 1/2006 | Song |
| 2006/0127924 A1 | 6/2006 | Hellyer et al. |

FOREIGN PATENT DOCUMENTS

| | | |
|---|---|---|
| WO | WO 9832018 A1 | 7/1998 |
| WO | WO 9927364 A1 | 6/1999 |
| WO | WO 0052464 A1 | 9/2000 |
| WO | WO 0062060 A2 | 10/2000 |
| WO | WO 0062060 A3 | 10/2000 |
| WO | WO 2004011906 A2 | 2/2004 |
| WO | WO 2004011906 A3 | 2/2004 |
| WO | WO 2005057214 A1 | 6/2005 |
| WO | WO 2006079826 A1 | 8/2006 |
| WO | WO 2007096637 A1 | 8/2007 |
| WO | WO 2007128980 A1 | 11/2007 |

OTHER PUBLICATIONS

Search Report and Written Opinion for PCT/US2006/016907, Apr. 18, 2007.
Search Report and Written Opinion for PCT/US2006/011188.
Abstract of Japanese Patent No. JP3210193.
Diavant Individual Test Areas from Roche Diagnostics, Inc., 2005, 2 pages.

* cited by examiner

FIG. 1

ENZYME DETECTION TECHNIQUE

BACKGROUND OF THE INVENTION

One of the most common bacterial infections is that of the urinary tract. Patients who need rapid diagnosis of urinary tract infections (UTIs) include premature newborn infants, prepubertal girls and young boys, sexually active women, elderly males and females, pre-operative patients, patients with chronic disease, patients with neurological disorders, patients with genitourinary congenital disorders including urethral valves and reflux, patients with sickle cell disease, patients with renal disease and polycystic kidney disease, patients having undergone renal transplantation and pregnant patients. The diagnosis of UTI in the elderly and in infants, in particular, is difficult because of different signs and symptoms and the inability to communicate.

One technique for diagnosing UTI involves measuring the level of pyuria (the presence of leukocytes in the urine). Leukocytes are normally present in urine, and careful studies have established that the threshold limit for pathological pyuria is about $1 \times 10^4$ leukocytes per milliliter of uncentrifuged urine. Pyuria correlates closely with acute symptomatic infection, and its presence may thus warrant further study of urine specimens in which microorganism counts are less than accepted threshold levels. Several methods have been developed for assessment of pyuria. One such method involves the detection of leukocyte esterase, which is an enzyme released by white blood cells. For example, dipsticks based on leukocyte esterase have been developed that contain an area predisposed with reagents. The test sample is spotted onto the area so that the enzyme reacts with the reagents, thereby inducing a color change. Unfortunately, such test methods generally require that a controlled reading window. However, it is not always feasible to carefully monitor testing, particularly in consumer-based applications.

As such, a need currently exists for an improved technique for detecting an enzyme in a test sample.

SUMMARY OF THE INVENTION

In accordance with one embodiment of the present invention, a diagnostic test kit for detecting the presence or absence of an enzyme (e.g., leukocyte esterase) within a test sample is disclosed. The test kit comprises a substrate that is capable of being cleaved in the presence of the enzyme to release a nucleophilic aromatic compound. The kit also comprises a lateral flow device that comprises a chromatographic medium. The chromatographic medium defines a detection zone within which is contained a first reagent (e.g., diazonium ion) that is capable of reacting with the nucleophilic aromatic compound to form a second reagent (e.g., aromatic azo compound). The second reagent exhibits a color that is different than the color of the first reagent. The lateral flow device also includes an absorbent material that receives the test sample after flowing through the chromatographic medium.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "test sample" generally refers to any material suspected of containing an enzyme. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the enzyme may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the enzyme.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a device for detecting the presence of an enzyme in a test sample. Various types of enzymes may be detected using the technique of the present invention, such as transferases, hydrolases, lyases, and so forth. In some embodiments, the enzyme of interest is a "hydrolase" or "hydrolytic enzyme", which refers to enzymes that catalyze hydrolytic reactions. Examples of hydrolytic enzymes include, but are not limited to, proteases (e.g., serine proteases, such as chymotrypsin, trypsin, elastase, and PSA; aspartic proteases, such as pepsin; thiol proteases, such as prohormone thiol proteases; metalloproteases; acid proteases; and alkaline proteases), peptidases (e.g., metallopeptidases or dipeptidylpeptidase I, II, or IV), lipases, nucleases, homo- or hetero-oligosaccharidases, homo- or hetero-polysaccharidases, phosphatases, sulfatases, neuraminidases, and esterases (e.g., acetylcholinesterase, acetylesterase, butyrylcholinesterase, cholesterol esterase, esterase, pectinesterase, phosphodiesterase, leukocyte esterase, etc.). In one particular embodiment, leukocyte esterase is detected to assist in the diagnosis of urinary tract infection.

The technique of the present invention employs a variety of reagents for detecting the presence of the enzyme. One such reagent is a substrate that is chemically acted upon or "cleaved" by the enzyme of interest to release a product. When detecting leukocyte esterase, for example, the substrate may be an ester that is catalytically hydrolyzed in the presence of leukocyte esterase to yield an aromatic compound. The aromatic esters may include, for instance, indoxyl esters having the following general formula:

wherein, R may be substituted or unsubstituted, and may be an alkyl group, an alkyoxy group, a hydroxyalkyl group, an alkylene group, a fatty acid group, and so forth. In addition, the aromatic rings may also be substituted or unsubstituted. Specific examples include, for instance, indoxyl acetate, indoxyl butyrate, indoxyl laureate, indoxyl stearate, indoxyl ester of a N-blocked amino acid or peptide and thioindoxyl analogs thereof, and N-Tosyl-L-alanine 3-indoxyl ester. Such indoxyl esters are hydrolyzed by the leukocyte esterase to form a benzopyrrole, such as indoxyl, which has the following structure:

Lactate esters may also be used in the present invention, such as described in U.S. Pat. No. 5,464,739 to Johnson, et al. and Pat. No. 5,663,044 to Noffsinger. et al., which are incorporated herein in their entirety by reference thereto for all purposes. Lactate esters are generally hydrolyzed by the leukocyte esterase to provide a hydroxy-pyrrole compound. Other suitable ester substrates include thiazole esters, pyrrole esters, thiophene esters, naphthyl esters, phenoxyl esters, quinolinyl esters, such as described in U.S. Pat. No. 5,750,359 to Huh, et al.; Pat. No. 4,657,855 to Corey, et al.; and Japanese Publication No. 03210193 to Kawanishi, et al., which are incorporated herein in their entirety by reference thereto for all purposes.

Still other suitable substrates for hydrolytic enzymes include, for instance, amides, peptides, ethers, or other chemical compounds having an enzymatically-hydrolyzable bond. Specific types of substrates may include proteins or glycoproteins, peptides, nucleic acids (e.g., DNA and RNA), carbohydrates, lipids, esters, derivatives thereof, and so forth. For instance, some suitable substrates for peptidases and/or proteases may include peptides, proteins, and/or glycoproteins, such as casein (e.g., β-casein, azocasein, etc.), albumin (e.g., bovine serum albumin), hemoglobin, myoglobin, keratin, gelatin, insulin, proteoglycan, fibronectin, laminin, collagen, elastin, and so forth. Still other suitable substrates are described in U.S. Pat. No. 4,748,116 to Simonsson, et al.; Pat. No. 5,786,137 to Diamond, et al.; Pat. No. 6,197,537 to Rao, et al.; and Pat. No. 6,235,464 to Henderson, et al.; Pat. No. 6,485,926 to Nemori, et al., which are incorporated herein in their entirety by reference thereto for all purposes.

If desired, the rate of the enzyme-catalyzed reaction may be selectively controlled using techniques known in the art, such as controlling the temperature, pH, substrate concentration, the presence of accelerators, the presence of inhibitors (competitive (binds to enzyme), uncompetitive (binds to enzyme-substrate complex), or noncompetitive (binds to enzyme and/or enzyme-substrate complex)), and so forth. These factors may be selectively controlled as desired to increase or decrease the reaction time. For example, an accelerator may be employed to enhance enzymatic activity. Suitable accelerators for hydrolytic esterases may include, for instance, pyridine, imidazole and their derivatives, metal complexes, and alcohols. Particularly useful alcohols are linear alcohols having 1 to 15 carbon atoms, such as decanol, undecanol and dodecanol. Other examples of suitable accelerators are described in U.S. Pat. No. 4,657,855 to Corey, et al. and Pat. No. 4,299,917 to Berger, et al., which are incorporated herein in their entirety by reference thereto for all purposes. The pH may also be selectively controlled to enhance enzyme activity and to inhibited unwanted side reactions. For instance, many ester substrates are unstable in highly basic or highly acidic conditions due to their tendency to hydrolyze. Thus, the pH is typically maintained at a relatively neutral level, such as from about 6 to about 9, and in some embodiments, about 7. Some biologically compatible buffers that may be used to maintain the desired pH include borate buffers, phosphate-buffered saline (PBS), 2-(N-morpholino) ethane sulfonic acid ("MES"), tris-hydroxymethylaminomethane ("Tris"), citrate buffers, and so forth.

Regardless of the manner in which the reaction is conducted, an aromatic compound is released through cleavage of the substrate that is capable of inducing a color change in the presence of certain reagents. The released aromatic compound is a nucleophile in that it contains a group that is electron rich (e.g., amine) and that may form bonds with electron deficient groups. For example, indoxyl esters are hydrolyzed by the leukocyte esterase to form indoxyl. Indoxyl contains an electron-rich, aromatic ring system that is capable of undergoing electrophilic attack by a diazonium ion having the generic formula:

The diazonium ion may be zwitterionic in that the counterion of the diazonium moiety is covalently bound to the ring system. The ring system of the diazonium ion may be substituted or unsubstituted. The ion may be provided by a variety of suitable diazonium salts, such as diazonium chlorides, diazonium acid sulphates, diazonium alkyl sulphates, diazonium fluoborates, diazonium benzenesulphonates, diazonium acid 1,5-naphthalenedisulphonates, and so forth. Specific examples of diazonium salts are 1-diazo-2-naphthol-4-sulfonate; 1-diazophenyl-3-carbonate; 4-diazo-3-hydroxy-1-naphthylsulfonate (DNSA); 4-diazo-3-hydroxy-7-nitro-1-naphthylsulfonate (NDNSA); 4-diazo-3-hydroxy-1,7-naphthyldisulfonate; 2-methoxy-4-(N-morpholinyl) benzene diazonium chloride; 4-diazo-3-hydroxy-7-bromo-1-naphthylsulfonate; and 4-diazo-3-hydroxy-7-[1,oxopropyl]-1-naphthylsulfonate. One particularly desired diazonium salt is 5-chloro-2-methoxybenzenediazonium chloride, which has a yellow color and is classified under the name "Diazo Red RC" or "Fast Red RC." More specifically, "Fast Red RC" has the following structure:

Other suitable diazonium salts are classified by the common names "Fast Red B" and "Fast Blue B." Still other suitable diazonium salts may be described in U.S. Pat. No. 4,637,979 to Skjold, et al.; Pat. No. 4,806,423 to Hugh, et al.; and Pat. No. 4,814,271 to Hugl, et al., which are incorporated herein in their entirety by reference thereto for all purposes.

As indicated above, the nucleophilic aromatic compounds released by the hydrolysis of the substrate are capable of undergoing electrophilic attack by a reagent (e.g., diazonium ion). This reaction is often referred to as "coupling" and results in the formation of another reagent having a different color. For example, diazonium ions may react with aromatic compounds to form an aromatic azo compound having the generic formula, R—N=N—R', wherein "R" and "R'" are aryl groups. Without intending to be limited by theory, it is believed that this reaction induces either a shift of the absorption maxima towards the red end of the spectrum ("bathochromic shift") or towards the blue end of the spectrum ("hypsochromic shift"). The type of absorption shift depends on the nature of the resulting azo molecule and whether it functions as an electron acceptor (oxidizing agent), in which a hypsochromic shift results, or whether it functions as an electron donor (reducing agent), in which a bathochromic shift results. Regardless, the absorption shift provides a color difference that is detectable, either visually or through instrumentation, to indicate the presence of leukocyte esterase or other enzymes within the test sample. For example, prior to contact with an infected test sample, the diazonium ion may be colorless or it may possess a certain color. However, after contacting the test sample and reacting with an aromatic compound released by hydrolysis of the substrate, an aromatic azo compound will form that exhibits a color that is different than the initial color of the diazonium ion. Exemplary aromatic azo compounds that may be formed include dimethyldiazene, diphenydiazene, 1-naphthyl-2-naphthyl diazene, 3-chlorophenyl-4-chlorophenyl diazene, methylvinyl diazene, and 2-naphthylphenyl diazene. In one particular embodiment, for instance, "Fast Red RC" (yellow), a diazonium ion, may react with indoxyl to form an aromatic azo compound that is red and has the following general structure (may be substituted or unsubstituted):

As a result of the color change, the presence of an enzyme (e.g., leukocyte esterase) in a test sample may be readily detected. The extent of the color change may be selectively controlled in accordance with the present invention to limit "false positives." More specifically, a small and perhaps normal amount of enzyme within a test sample may hydrolyze a substrate to release a nucelophilic aromatic compound. In some cases, however, the released aromatic compound may undergo an oxidation reaction if left in air or other oxidizing environment for too great a period of time. For example, indoxyl may be oxidized to form indigo, which is blue and has the following structure:

The resulting blue color of indigo may indicate a "false positive" or at the very least, adversely affect the ability to semi-quantitatively or quantitatively determine the presence of the enzyme. Thus, the present inventor has discovered a technique for reducing the problem of such "false positives." Instead of simply measuring the results after a certain period of time, the desired reaction time may be achieved by selectively controlling the medium in which the reaction occurs. That is, the reaction medium is chromatographic in nature such that the enzyme and substrate are allowed to flow in a consistent and controllable manner. While flowing through the medium, the enzyme and substrate react to release an aromatic product that subsequently couples with a diazonium ion to form an aromatic azo compound. The aromatic azo compound is immobilized within a discrete detection region for analysis. Due to the nature of the controlled fluid flow, any unreacted substrate travels to the end of the reaction medium so that it is unable to adversely interfere with observance of the aromatic azo compound in the detection region. Thus, to the extent that subsequent oxidation of aromatic compounds that are not captured at the detection region, the resulting color change will not occur within the detection region.

Figure 1:
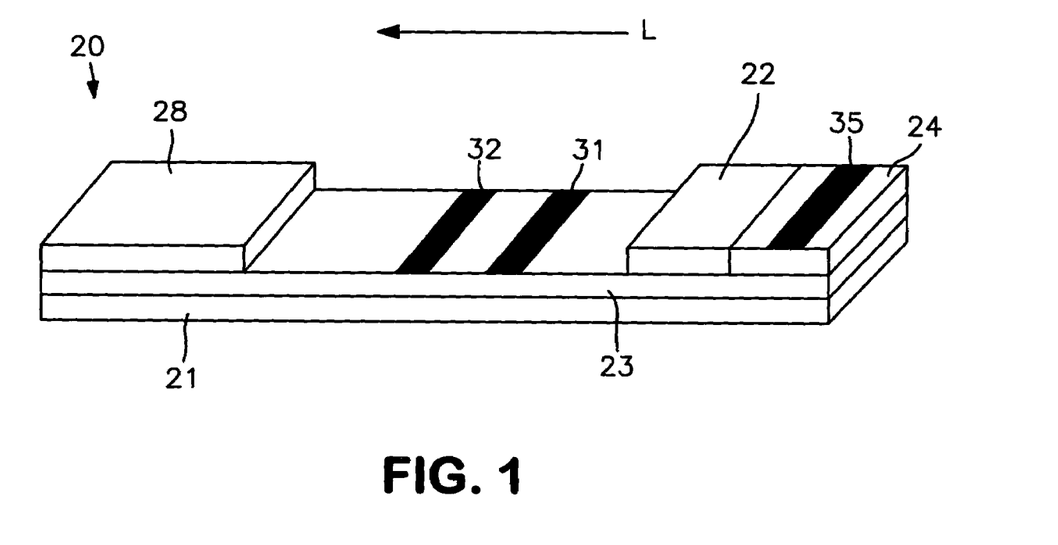
FIG. 1 is a perspective view of one embodiment of a lateral flow device that may be used in the present invention.

Various embodiments for accomplishing the detection of the enzyme using fluid flow control techniques will now be described in more detail. Referring to FIG. 1, for instance, one embodiment of a lateral flow device 20 that may be formed according to the present invention will now be described in more detail. As shown, the device 20 contains a chromatographic medium 23 optionally supported by a rigid support material 21. In general, the chromatographic medium 23 may be made from any of a variety of materials through which the test sample is capable of passing. For example, the chromatographic medium 23 may be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium 23 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 21 carries the chromatographic medium 23. For example, the support 21 may be positioned directly adjacent to the chromatographic medium 23 as shown in FIG. 1, or one or more intervening layers may be positioned between the chromatographic medium 23 and the support 21. Regardless, the support 21 may generally be formed from any material able to carry the chromatographic medium 23. The support 21 may be formed from a material that is transmissive to light, such as transparent or optically diffuse (e.g., transluscent) materials. Also, it is generally desired that the support 21 is liquid-impermeable so that fluid flowing through the medium 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 23, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

The device 20 also contains an absorbent material 28 that is positioned adjacent to the medium 23. The absorbent material 28 assists in promoting capillary action and fluid flow through the medium 23. In addition, the absorbent material 28 receives fluid that has migrated through the entire chromatographic medium 23 and thus draws any unreacted components away from the detection region to help reduce the likelihood of "false positives." Some suitable absorbent materials that may be used in the present invention include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

To initiate the detection of the enzyme within the test sample, a user may directly apply the test sample to a portion of the chromatographic medium 23 through which it may then travel in the direction illustrated by arrow "L" in FIG. 1. Alternatively, the test sample may first be applied to a sample application zone 24 that is in fluid communication with the chromatographic medium 23. The sample application zone 24 may be formed on the medium 23. Alternatively, as shown in FIG. 1, the sample application zone 24 may be formed by a separate material, such as a pad. Some suitable materials that may be used to form such sample pads include, but are not limited to, nitrocellulose, cellulose, porous polyethylene pads, and glass fiber filter paper. If desired, the sample application zone 24 may also contain one or more pretreatment reagents, either diffusively or non-diffusively attached thereto. In the illustrated embodiment, the test sample travels from the sample application zone 24 to a reagent zone 22 that is in communication with the sample application zone 24. As described above, the reagent zone 22 may be formed on the medium 23. Alternatively, as shown in FIG. 1, the reagent zone 22 is formed from a separate material or pad. Such a reagent pad may be formed from any material through which the test sample is capable of passing, such as glass fibers. To facilitate detection of the enzyme in the manner described above, a substrate is employed. In some embodiments, the substrate may be mixed with the test sample prior to application to the device 20. Alternatively, the substrate may be diffusively immobilized on the device 20 prior to application of the test sample. Such pre-application provides a variety of benefits, including the elimination of the need for a subsequent user to handle and mix the reagents with the test sample or a diluent. This is particularly useful in point-of-care applications when the user is not generally a trained lab technician or medical professional. The substrate may be disposed downstream from the sample application zone 24. In this manner, the test sample is capable of mixing with the enzyme upon application. Alternatively, the substrate may be positioned upstream from the sample application zone 24. For instance, a diluent may be employed to induce mixing between the substrate and test sample.

If desired, the pH may be maintained at a relatively neutral level to facilitate the desired enzyme-catalyzed reaction, such as described above. To accomplish the desired pH level, a buffer may be mixed with the substrate prior to application to the device 20, mixed with the test sample, or both. Alternatively, the buffer may be separately applied to the lateral flow device 20 so that it is capable of mixing with the reagents upon application to the test sample.

Referring again to FIG. 1, the lateral flow device 20 includes a detection zone 31 within which is immobilized a diazonium ion, such as described above. The diazonium ion may be applied directly to the medium 23 or first formed into a solution prior to application. Various solvents may be utilized to form the solution, such as, but not limited to, acetonitrile, dimethylsulfoxide (DMSO), ethyl alcohol, dimethylformamide (DMF), and other polar organic solvents. For instance, the amount of a diazonium salt in the solution may range from about 0.001 to about 100 milligrams per milliliter of solvent, and in some embodiments, from about 0.1 to about 10 milligrams per milliliter of solvent. In one particular embodiment, the detection zone 31 is defined by the chromatographic medium 23 and formed by coating a solution thereon using well-known techniques and then dried. The diazonium ion concentration may be selectively controlled to provide the desired level of detection sensitivity.

Typically, it is desired that the diazonium ion be applied in a manner so that it does not substantially diffuse through the matrix of the chromatographic medium 23 (i.e., non-diffusively immobilized). This enables a user to readily detect the change in color that occurs upon reaction of the diazonium ion with a nucleophilic aromatic compound. The diazonium ion may form an ionic and/or covalent bond with functional groups present on the surface of the chromatographic medium 23 so that it remains immobilized thereon. For instance, particles, such as described below, may facilitate the immobilization of the diazonium ion at the detection zone 31. Namely, the diazonium ion may be coated onto particles, which are then immobilized on the chromatographic medium 23 of the device 20. In this manner, the diazonium ion is able to readily contact nucleophilic aromatic compounds flowing through the medium 23.

One benefit of the lateral flow device of the present invention is its ability to readily incorporate one or more additional reagent zones to facilitate the above-described enzyme-catalyzed reaction. For example, referring again to FIG. 1, one such zone is a quenching zone 35. The quenching zone 35 is configured to remove compounds from the test sample that would otherwise interfere with the accuracy of the detection system. For example, contaminants within the test sample (e.g., phenolics, bilirubin, urobilinogen, etc.) may react with the diazonium ion within the detection zone 31 and form an aromatic azo compound, thereby producing a "false negative" result. Thus, the quenching zone 35 may contain a quenching agent, such as a diazonium ion, that is capable of reacting with the reaction contaminants. The quenching agent may be the same or different than the detection agent used within the detection zone 31. Typically, the quenching agent is non-diffusively immobilized within the quenching zone 35 in the manner described above so that it does not flow through the medium 23 and interfere with testing. The location of the quenching zone 35 may vary, but is typically positioned upstream from the detection zone 31 and the location at which the substrate is applied to avoid interference with enzyme detection. For example, in the illustrated embodiment, the quenching zone 35 is positioned between the sample application zone 24 and the reagent zone 22. Alternatively, the quenching zone 35 may be positioned upstream from the sample application zone 24.

Another zone that may be employed in the lateral flow device 20 for improving detection accuracy is a control zone 32. The control zone 32 gives a signal to the user that the test is performing properly. More specifically, control reagents may be employed that flow through the chromatographic medium 23 upon contact with a sufficient volume of the test sample. These control reagents may then be observed, either visually or with an instrument, within the control zone 32. The control reagents generally contain a detectable substance, such as luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and Pat. No. 5,252,459 to Tarcha. et al., which are incorporated herein in their entirety by reference thereto for all purposes.

If desired, the detectable substances may be disposed on particles (sometimes referred to as "beads" or "microbeads"). Among other things, the particles enhance the ability of the detectable substance to travel through a chromatographic medium. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. Commercially available examples of suitable particles include fluorescent carboxylated microspheres sold by Molecular Probes, Inc. under the trade names "FluoSphere" (Red 580/605) and "Transfluo-Sphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

The location of the control zone 32 may vary based on the nature of the test being performed. In the illustrated embodiment, for example, the control zone 32 is defined by the chromatographic medium 23 and positioned downstream from the detection zone 31. In such embodiments, the control zone 32 may contain a material that is non-diffusively immobilized in the manner described above and forms a chemical and/or physical bond with the control reagents. When the control reagents contain latex particles, for instance, the control zone 32 may include a polyelectrolyte that binds to the particles. Various polyelectrolytic binding systems are described, for instance, in U.S. Patent App. Publication No. 2003/0124739 to Song, et al., which is incorporated herein in it entirety by reference thereto for all purposes. In alternative embodiments, however, the control zone 32 may simply be defined by a region of the absorbent material 28 to which the control reagents flow after traversing through the chromatographic medium 23.

Regardless of the particular control technique selected, the application of a sufficient volume of the test sample to the device 20 will cause a signal to form within the control zone 32, whether or not the enzyme is present. Among the benefits provided by such a control zone is that the user is informed that a sufficient volume of test sample has been added without requiring careful measurement or calculation. This provides the ability to use the lateral flow device 20 without the need for externally controlling the reaction time, test sample volume, etc.

In addition to the zones specified above, the lateral flow device 20 may also include other optional zones. For example, in one embodiment, the lateral flow device 20 may include an accelerator zone (not shown) in which is contained an accelerator for the enzyme-catalyzed substrate reaction. Typically, the accelerator is diffusively immobilized within the accelerator zone in the manner described above so that it may flow through the medium 23 upon contact with the test sample. The location of the accelerator zone may generally vary, so long as it positioned upstream from the detection zone 31. For example, in some embodiments, the accelerator zone may be positioned at a location (e.g., sample application zone 24) that is upstream from the application of the substrate (e.g., 10 reagent zone 24). Due to the separation provided between the substrate and accelerator, the likelihood of any premature reaction therebetween is thus reduced. It should be understood, however, that the accelerator may nevertheless be combined with the substrate in some applications.

The detection zone 31, quenching zone 35, control zone 32, accelerator zone, and any other zone employed in the lateral flow device 20 may generally provide any number of distinct detection regions so that a user may better determine the concentration of the enzyme within the test sample. Each region may contain the same or different materials. For example, the zones may include two or more distinct regions (e.g., lines, dots, etc.). The regions may be disposed in the form of lines in a direction that is substantially perpendicular to the flow of the test sample through the device 20. Likewise, in some embodiments, the regions may be disposed in the form of lines in a direction that is substantially parallel to the flow of the test sample through the device 20.

One particular embodiment of a method for detecting the presence of leukocyte esterase within a test sample using the device 20 of FIG. 1 will now be described in more detail. Initially, a test sample containing leukocyte esterase is applied to the sample application zone 24 and travels in the direction "L" to the reagent zone 22. At the reagent zone 22, the esterase is able to mix with and begin to initiate the catalytic reaction. As the mixture flows through the device 20, the esterase hydrolyzes the ester bonds of the substrate and releases nucleophilic aromatic compounds. The aromatic compounds then flow to the detection zone 31 where they react with a diazonium ion to form a colored azo compound. After the reaction, the detection zone 31 changes color. Thus, the color or color intensity of the detection zone 31 may be determined, either visually or with instrumentation. If desired, the intensity of the color at the detection zone 31 may be measured to quantitatively or semi-quantitatively determine the level of enzyme present in the test sample. The intensity of the color at the detection zone 31 is typically directly proportional to enzyme concentration. The intensity of the detection signal "$I_s$" produced at the detection zone 31 may also be compared to a predetermined detection curve developed for a plurality of known enzyme concentrations. To determine the quantity of enzyme in an unknown test sample, the signal may simply be converted to enzyme concentration according to the detection curve. Regardless, the esterase and any unreacted substrate and/or aromatic compounds then travel past the detection zone 31 until they reach the absorbent material 28. In some cases, the aromatic compounds will oxidize over a period of time in air to form colored compounds. However, because such colored compounds are not located at the detection region 31, they generally do not interfere with the detection accuracy.

The present invention provides a relatively simple, compact and cost-efficient device for accurately detecting the presence of certain enzymes (e.g., leukocyte esterase) within a test sample (e.g., urine). The test result may be visible so that it is readily observed by the person performing the test in a prompt manner and under test conditions conducive to highly reliable and consistent test results. The test is also less time-dependent.

The present invention may be better understood with reference to the following example.

EXAMPLE

The ability to detect leukocyte esterase in accordance with the present invention was demonstrated. Initially, an HF12002 nitrocellulose membrane laminated to a support card (Millipore, Inc.) was provided as the chromatographic medium. To form a detection zone, Diazo Red DC (DR) was initially striped by hand onto the membrane. The Diazo Red DC was in the form of a solution containing water and approximately 15 wt. % dimethylformamide ("DMF"). The membrane was then dried at 37° C. for two hours. A reagent pad was then fabricated from a glass fiber pad having a length of 15 centimeters (Millipore Inc.). More specifically, the pad was soaked with 15 milliliters of a mixture containing (i) 1 wt. % Tween 20 (available from Sigma-Aldrich Chemical Co.) in 20 millimolar Tris buffer (pH=7.4); (ii) 0.5 milliliters of a solution containing 20 wt. % sucrose; and (iii) 0.2 milliliters of indoxyl acetate (0.1 molar in DMF). The glass fiber pad was then dried at 37° C. for two hours and laminated on one side of the membrane. A cellulose pad was laminated to the other side of the membrane card to provide an absorbent or wicking pad. A sample application pad was then laminated to the glass fiber pad to provide a sample application zone. The fully assembled card was cut into 4-millimeter wide strip devices.

To test the device, a control sample (in Tris buffer, pH=7.4, 20 millimolar) and a positive esterase sample (10 micrograms per milliliter, in Tris buffer, pH=7.4, 20 millimolar) were prepared. The esterase was derived from porcine liver crude and obtained from Sigma-Aldrich Chemical Co. of St. Louis, Mo. 150 microliters of each sample were then applied to the sample application zone of two separate devices. After approximately 15 minutes, each sample was visually observed. For the control sample, the detection zone remained yellow; however, for the positive esterase sample, the detection zone was red.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diagnostic test kit for detecting the presence or absence of an enzyme within a test sample, the test kit comprising:

a substrate that is capable of being cleaved in the presence of the enzyme to release a nucleophilic aromatic compound; and a lateral flow device that comprises:

a chromatographic medium defining a discrete detection zone within which is contained a first reagent, wherein the nucleophilic aromatic compound is capable of flowing through the chromatographic medium and reacting with the first reagent within the detection zone to form a second reagent, the second reagent exhibiting a color that is different than the color of the first reagent; and an absorbent material positioned adjacent to the chromatographic medium and located downstream from the detection zone, wherein the absorbent material receives the test sample after flowing through the chromatographic medium.

2. The diagnostic test kit of claim 1, wherein the enzyme is an esterase.

3. The diagnostic test kit of claim 2, wherein the esterase is leukocyte esterase.

4. The diagnostic test kit of claim 2, wherein the substrate is an aromatic ester.

5. The diagnostic test kit of claim 4, wherein the substrate is an indoxyl ester, lactate ester, thiazole ester, pyrrole ester, thiophene ester, naphthyl ester, phenoxyl ester, or quinolinyl ester.

6. The diagnostic test kit of claim 1, wherein the nucleophilic aromatic compound is a benzopyrrole.

7. The diagnostic test kit of claim 1, wherein the first reagent is a diazonium ion.

8. The diagnostic test kit of claim 7, wherein the diazonium ion is provided by a salt selected from the group consisting of diazonium chlorides, diazonium acid sulphates, diazonium alkyl sulphates, diazonium fluoborates, diazonium benzenesulphonates, and diazonium acid 1,5-naphthalenedisulphonates.

9. The diagnostic test kit of claim 7, wherein the second reagent is an aromatic azo compound.

10. The diagnostic test kit of claim 1, wherein the chromatographic medium is a porous membrane.

11. The diagnostic test kit of claim 1, wherein the substrate is disposed on the lateral flow assay device.

12. The diagnostic test kit of claim 11, wherein the lateral flow assay device further comprises a reagent zone within which is contained the substrate.

13. The diagnostic test kit of claim 12, further comprising a sample application zone that is located upstream from the reagent zone.

14. The diagnostic test kit of claim 1, wherein the lateral flow device comprises a quenching zone located upstream from the detection zone.

15. The diagnostic test kit of claim 14, wherein the quenching zone contains an agent capable of reacting with a contaminant in the test sample.

16. The diagnostic test kit of claim 1, wherein the lateral flow device comprises a control zone that is capable of signaling the presence of the test sample.

17. The diagnostic test kit of claim 16, further comprising a control reagent that is capable being detected within the control zone.

18. The diagnostic test kit of claim 1, wherein the test kit further comprises an accelerator for the substrate.

19. The diagnostic test kit of claim 18, wherein the accelerator is contained within an accelerator zone located upstream from the detection zone.

20. The diagnostic test kit of claim 1, wherein the test sample is urine.

21. A diagnostic test kit for detecting the presence or absence of leukocyte esterase within urine, the test kit comprising:

an aromatic ester substrate that is capable of being hydrolyzed in the presence of leukocyte esterase to release a nucleophilic aromatic compound; and a lateral flow device that comprises:

a porous membrane defining a discrete detection zone within which is contained a diazonium ion, wherein the nucleophilic aromatic compound is capable of flowing through the chromatographic medium and reacting with the diazonium ion within the detection zone to form an aromatic azo compound, the aromatic azo compound exhibiting a color that is different than the color of the diazonium ion; and an absorbent material positioned adjacent to the porous membrane and located downstream from the detection zone, wherein the absorbent material receives the urine after flowing through the porous membrane.

22. The diagnostic test kit of claim 21, wherein the substrate is an indoxyl ester, lactate ester, thiazole ester, pyrrole ester, thiophene ester, naphthyl ester, phenoxyl ester, or quinolinyl ester.

23. The diagnostic test kit of claim 21, wherein the nucleophilic aromatic compound is a benzopyrrole.

24. The diagnostic test kit of claim 21, wherein the diazonium ion is provided by a salt selected from the group consisting of diazonium chlorides, diazonium acid sulphates, diazonium alkyl sulphates, diazonium fluoborates, diazonium benzenesulphonates, and diazonium acid 1,5-naphthalenedisulphonates.

25. The diagnostic test kit of claim 21, wherein the substrate is disposed on the lateral flow assay device.

26. The diagnostic test kit of claim 25, wherein the lateral flow assay device further comprises a reagent zone within which the substrate is disposed.

27. The diagnostic test kit of claim 26, further comprising a sample application zone that is positioned upstream from the reagent zone.

28. The diagnostic test kit of claim 21, wherein the lateral flow device comprises a quenching zone located upstream from the detection zone.

29. The diagnostic test kit of claim 21, wherein the lateral flow device comprises a control zone that is capable of signaling the presence of the urine.

30. The diagnostic test kit of claim 21, wherein the test kit further comprises an accelerator for the substrate, the accelerator being contained within an accelerator zone located upstream from the detection zone.

31. The diagnostic test kit of claim 1, wherein the absorbent material includes nitrocellulose, a cellulosic material, a porous polyethylene pad, glass fiber filter paper, or a combination thereof.

32. The diagnostic test kit of claim 21, wherein the absorbent material includes nitrocellulose, a cellulosic material, a porous polyethylene pad, glass fiber filter paper, or a combination thereof.

33. The diagnostic test kit of claim 1, wherein the lateral flow device further comprises a reagent pad on which the substrate is disposed.

34. The diagnostic test kit of claim 33, wherein the lateral flow device further comprises a sample pad configured to receive the test sample.

35. The diagnostic test kit of claim 34, wherein the sample pad also defines a quenching zone that contains an agent capable of reacting with a contaminant in the test sample.

36. The diagnostic test kit of claim 21, wherein the lateral flow device further comprises a reagent pad on which the substrate is disposed.

37. The diagnostic test kit of claim 36, wherein the lateral flow device further comprises a sample pad configured to receive the test sample.

38. The diagnostic test kit of claim 37, wherein the sample pad also defines a quenching zone that contains an agent capable of reacting with a contaminant in the test sample.

* * * * *